United States Patent
Cho et al.

(10) Patent No.: US 10,034,652 B2
(45) Date of Patent: Jul. 31, 2018

(54) DETECTOR ASSEMBLY, COMPUTED TOMOGRAPHY APPARATUS HAVING THE SAME AND CONTROL METHOD FOR THE SAME

(71) Applicant: SAMSUNG ELECTRONICS CO., LTD., Suwon-si (KR)

(72) Inventors: Min Kook Cho, Hwaseong-si (KR); Byung Sun Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 171 days.

(21) Appl. No.: 14/823,006

(22) Filed: Aug. 11, 2015

(65) Prior Publication Data

US 2016/0183906 A1  Jun. 30, 2016

(30) Foreign Application Priority Data

Dec. 30, 2014  (KR) .................. 10-2014-0194084

(51) Int. Cl.
  *A61B 6/00*  (2006.01)
  *A61B 6/03*  (2006.01)
  *G06T 5/00*  (2006.01)
  *G06T 7/00*  (2017.01)

(52) U.S. Cl.
  CPC ............. *A61B 6/585* (2013.01); *A61B 6/032* (2013.01); *A61B 6/4241* (2013.01); *A61B 6/4035* (2013.01); *A61B 6/52* (2013.01)

(58) Field of Classification Search
  CPC .............................. A61B 6/4241; A61B 6/585
  See application file for complete search history.

(56) References Cited

U.S. PATENT DOCUMENTS

| 5,764,719 | A  | * | 6/1998  | Noettling | ............... | A61B 6/032 |
|-----------|----|---|---------|-----------|---|---|
|           |    |   |         |           |   | 348/E5.079 |
| 7,433,443 | B1 |   | 10/2008 | Tkaczyk et al. | | |
| 7,613,274 | B2 | * | 11/2009 | Tkaczyk   | ............... | A61B 6/032 |
|           |    |   |         |           |   | 378/19 |
| 8,628,241 | B2 | * | 1/2014  | Kappler   | ................ | A61B 6/032 |
|           |    |   |         |           |   | 378/18 |

(Continued)

FOREIGN PATENT DOCUMENTS

| JP | 2014-210180 A   | 11/2014 |
|----|-----------------|---------|
| KR | 10-1998-0008174 A | 4/1998 |
| KR | 10-2014-0024844 A | 3/2014 |

OTHER PUBLICATIONS

Communication dated Jul. 1, 2016, issued by the Korean Intellectual Property Office in counterpart Korean Application No. 10-2014-0194084.

*Primary Examiner* — David J Makiya
*Assistant Examiner* — Soorena Kefayati
(74) *Attorney, Agent, or Firm* — Sughrue Mion, PLLC

(57) ABSTRACT

A computed tomography (CT) apparatus includes an X-ray source configured to generate X-rays; and a detector which is configured to detect the X-rays radiated by the X-ray source, and includes a counting detection region configured to generate X-ray data corresponding to the detected X-rays according to a photon counting method, and an integrative detection region which is configured to generate the X-ray data corresponding to the detected X-rays according to a charge integration method, and is formed on an outer portion of the counting detection region with respect to a rotation axis of a gantry.

9 Claims, 18 Drawing Sheets

(56) References Cited

U.S. PATENT DOCUMENTS

| | | | |
|---|---|---|---|
| 9,036,786 B2* | 5/2015 | Parsons | H01J 35/08 378/121 |
| 9,310,495 B2* | 4/2016 | Spartiotis | G01T 1/247 |
| 9,579,075 B2* | 2/2017 | Besson | G01T 1/2985 |
| 9,615,812 B2* | 4/2017 | Herrmann | A61B 6/42 |
| 9,724,056 B2* | 8/2017 | Zamyatin | A61B 6/4241 |
| 2007/0205367 A1* | 9/2007 | Deman | G01T 1/2985 250/363.02 |
| 2011/0211667 A1* | 9/2011 | Ikhlef | A61B 6/032 378/19 |
| 2012/0300897 A1* | 11/2012 | Flohr | A61B 6/4014 378/9 |
| 2013/0200269 A1 | 8/2013 | Abraham et al. | |
| 2013/0301799 A1* | 11/2013 | Kang | A61B 6/5258 378/62 |
| 2014/0093994 A1 | 4/2014 | Bui et al. | |
| 2015/0146844 A1* | 5/2015 | Zamyatin | A61B 6/032 378/5 |

* cited by examiner

DETECTOR ASSEMBLY, COMPUTED TOMOGRAPHY APPARATUS HAVING THE SAME AND CONTROL METHOD FOR THE SAME

CROSS-REFERENCE TO RELATED APPLICATION

This application claims priority from Korean Patent Application No. 10-2014-0194084, filed on Dec. 30, 2014, in the Korean Intellectual Property Office, the disclosure of which is incorporated herein by reference in its entirety.

BACKGROUND

1. Field

Apparatuses and methods consistent with exemplary embodiments relate to a detector assembly for imaging an object by detecting X-rays, a computed tomography apparatus having the same and control method for the same, and more particularly, to a detector assembly having a combination of a photon counting detector and a charge integration detector, a computed tomography apparatus having the same and control method for the same.

2. Description of Related Art

An X-ray imaging apparatus irradiates X-rays onto an object, and analyzes the X-rays that pass through the object, thereby identifying an inner structure of the object. Since the transmittance of X-rays varies depending on tissues of the object, an inner structure of the object can be imaged by using an attenuation coefficient obtained by digitizing the transmittance.

An X-ray imaging apparatus may include a radiography apparatus acquiring a projection image by transmitting X-rays in one direction and a computed tomography (CT) apparatus reconstructing an image by using a computer by transmitting X-rays in various directions.

SUMMARY

One or more exemplary embodiments provide a detector assembly capable of effectively using the advantage of each detection regions and capable of improving response characteristics of the detector by including detection regions different from each other (an integrative detection region a counting detection region), a computed tomography (CT) apparatus having the same and a control method for the same.

In accordance with an aspect of an exemplary embodiment, a CT apparatus includes a rotatable gantry in which an X-ray source generating and irradiating X-rays, and a detector detecting X-rays incident from the X-ray source are mounted to face each other, wherein the detector may include an integrative detection region generating X-ray data corresponding to the detected X-rays according to a charge integration method and a counting detection region formed on an inner or outer portion of the integrative detection region with respect to a rotation axis of the gantry, and generating X-ray data corresponding to the detected X-rays according to a photon counting method.

The detector may include a plurality of detection modules arranged in a direction perpendicular to the rotation axis, wherein the plurality of detection modules may include an integrative detection region generating X-ray data according to a charge integration method and a counting detection region formed on an inner or outer portion of the integrative detection region with respect to a rotation axis of the gantry, and generating X-ray data according to a photon counting method.

The plurality of detection modules may include a plurality of detector elements arranged in two dimensional (2D) matrices.

A detector element, which is disposed on the integrative detection region, among the plurality of detector elements may generate X-ray data according to a charge integration method.

A detector element, which is disposed on the counting detection region, among the plurality of detector elements may generate X-ray data according to a photon counting method.

The CT apparatus may further include a filter mounted between the X-ray source and the detector, and formed in a way that at least one of a thickness and material in a direction perpendicular to the rotation axis may be altered.

The CT apparatus may further include an image processor correcting X-ray data generated by the counting detection region by using X-ray data generated by the integrative detection region.

The image processor may use X-ray data generated by an integrative detection region on which X-ray, having the same beam quality as that of X-ray incident on the counting detection region, is incident.

The counting detection region may detect the incident X-ray, and may generate X-ray data corresponding to the detected X-ray by dividing the detected X-ray according to a predetermined plurality of energy bands.

A detector element placed in the counting detection region may include a plurality of comparators and a plurality of counters both of which are corresponding to the plurality of energy bands.

In accordance with an aspect of an exemplary embodiment, a detector assembly includes a detector generating X-ray data by detecting an incident X-ray and a data obtainer converting the generated X-ray data into a digital form and outputting the digital form, wherein the detector may include an integrative detection region generating X-ray data corresponding to the detected X-rays according to a charge integration method and a counting detection region formed on an inner portion or an outer portion of the integrative detection region with respect to a rotation axis of a gantry to which the detector assembly is mounted, and generating X-ray data corresponding to the detected X-rays according to a photon counting method.

The detector may include a plurality of detection modules arranged in a direction perpendicular to the rotation axis, wherein the plurality of detection modules may include an integrative detection region generating X-ray data according to a charge integration method and a counting detection region formed on an inner or outer portion of the integrative detection region with respect to a rotation axis of the gantry, and generating X-ray data according to a photon counting method.

The plurality of detection modules may include a plurality of detector elements arranged in 2D matrices.

A detector element, which is disposed on the integrative detection region, among the plurality of detector elements may generate X-ray data according to a charge integration method.

A detector element, which is disposed on the counting detection region, among the plurality of detector elements may generate X-ray data according to a photon counting method.

The counting detection region may detect the incident X-ray, and may generate X-ray data corresponding to the detected X-ray by dividing the detected X-ray according to a predetermined plurality of energy bands.

A detector element placed in the counting detection region may include a plurality of comparators and a plurality of counters both of which are corresponding to the plurality of energy bands.

In accordance with an aspect of an exemplary embodiment, a control method of a CT apparatus including a detector in which a counting detection region is disposed on the center with respect to a rotation axis of a gantry, and an integrative detection region is disposed on an upper portion or a lower portion of the counting detection region includes acquiring X-ray data from the integrative detection region, acquiring X-ray data from the counting detection region, and correcting X-ray data acquired from the counting detection region by using X-ray data acquired from the integrative detection region.

The correcting of X-ray data may include calculating a calibration function representing a relation between X-ray data acquired by the integrative detection region and X-ray data acquired by the counting detection region.

The correcting of X-ray data may include using X-ray data generated by X-ray having the same beam quality to each other among X-ray incident on the counting detection region and X-ray incident on the integrative detection region.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
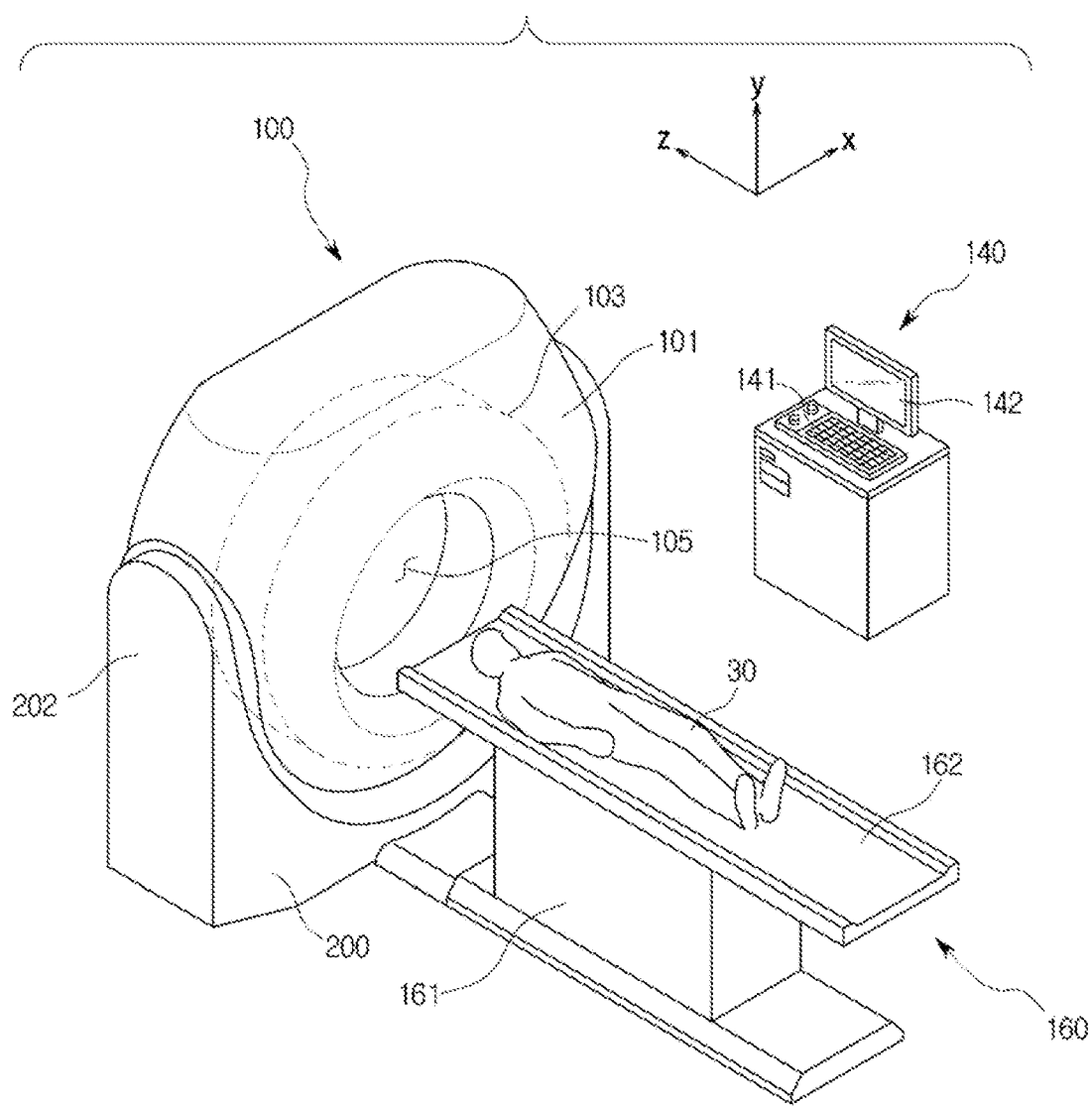
FIG. 1 is a view illustrating a computed tomography (CT) apparatus according to an exemplary embodiment.

Certain exemplary embodiments are described in greater detail below with reference to the accompanying drawings.

In the following description, the same drawing reference numerals are used for the same elements even in different drawings. Thus, description of the same elements is not repeated. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Figure 2:
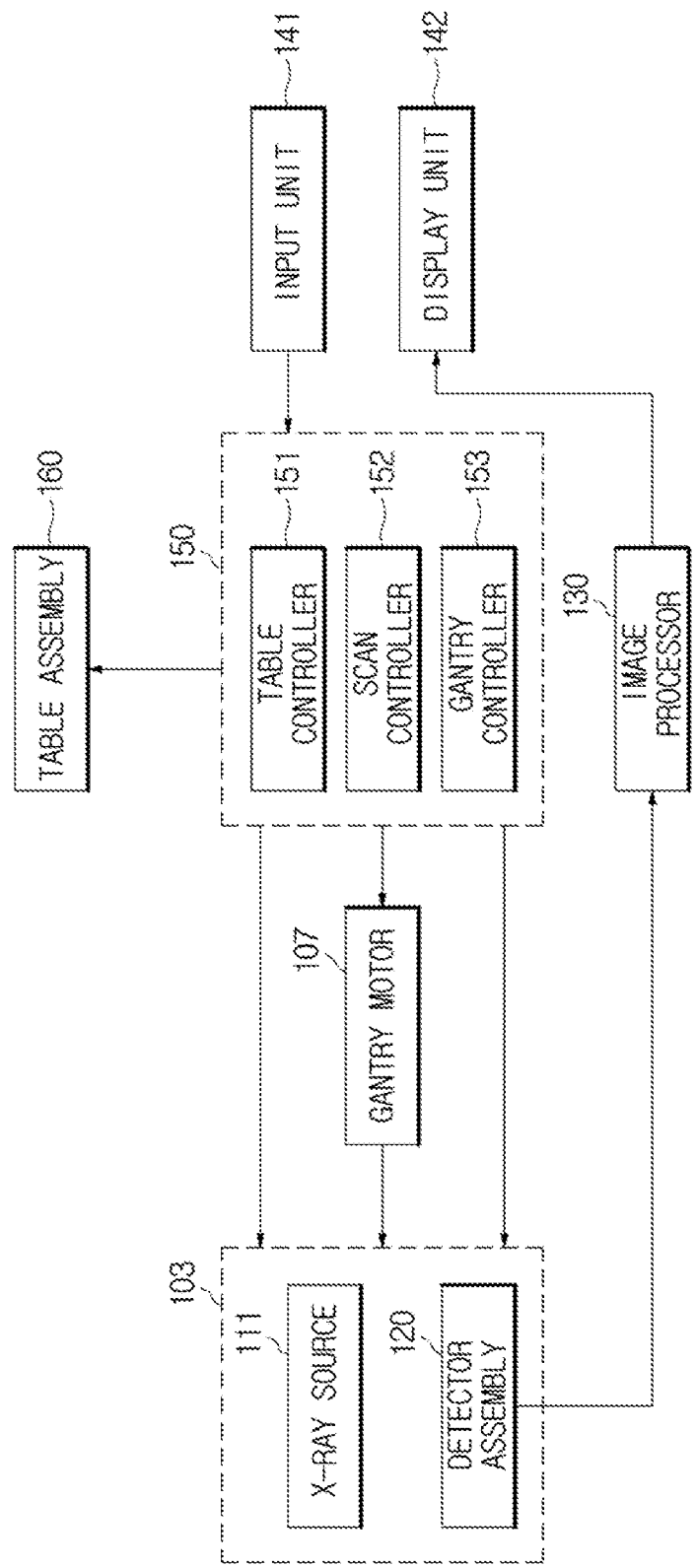
FIG. 2 is a control block diagram illustrating a CT apparatus according to an exemplary embodiment.

FIG. 1 is a view illustrating a computed tomography (CT) apparatus according to an exemplary embodiment, and FIG. 2 is a control block diagram illustrating a CT apparatus according to an exemplary embodiment.

Referring to FIG. 1, a gantry 103 is provided inside a housing 101 of a CT apparatus 100 in accordance with an exemplary embodiment, and an X-ray source 111 (refer to FIG. 3), and a detector assembly 120 are mounted to be face each other inside the gantry 103 so that the detector assembly 120 (refer to FIG. 3) detects X-rays irradiated from the X-ray source 111.

An object 30 may be placed on a table assembly 160, and a patient table where the object 30 is placed may be supported by a table support 161. A driving device, such as a motor, a gear, and the like may be provided inside the table support 161 to supply driving force to the patient table 162.

When the patient table 162 is moved toward a bore 105 in a Z-axis direction, the object 30 may be placed in the bore 105, and when the gantry 103 is rotated in a case when the object 30 is placed in the bore 105, the X-ray source 111 may emit X-rays while the gantry 103 is rotated and the X-ray source 111 rotates around the object 30 with 360 degree (1 rotation) or more. Therefore, the emitted X-rays may be passed through the object 30 and may be detected by the detector assembly 120.

The CT apparatus 100 may be provided with a work station 140 having a user interface for providing information to a user and receiving a control command from the user.

Referring to FIG. 2, the CT apparatus 100 in accordance with an exemplary embodiment includes the X-ray source 111 generating X-rays having a certain energy band and emitting the X-rays to an object, the detector assembly 120 acquiring X-ray data by detecting X-rays passed through the object, a controller 150 controlling a rotation of the gantry 103, the X-ray source and the detector assembly 120 both of which are mounted to the gantry 103, and the table assembly 160, an image processor 130 generating a CT image by reconstructing the acquired X-ray data, an input unit 141 receiving a command related to a control of the CT apparatus 100 from a user, and a display 142 displaying a screen related to a control of the CT or a CT image of the object.

The X-ray source 111 generates X-rays having a certain energy band and emits the X-rays and the detector assembly 120 detects the X-rays and converts the X-rays to X-ray data, and then transmits the X-ray data to the image processor 130.

The image processor 130 may reconstruct a CT image, which is imaging the inside of the object, by using the X-ray data transmitted from the detector assembly 120. The method of reconstructing an image may include interactive method, direct Fourier method, filtered back projection method, and the like.

In addition, the image processor 130 may correct data acquired by a counting detection region by using data acquired by an integrative detection region, a description thereof will be described later.

The CT image reconstructed by the image processor 130 is transmitted to the display 142, and the display 142 displays the CT image of the object.

The input unit 141 and the display 142 may be provided in the work station 140. The input unit 141 may be realized by at least one of a mouse, a keyboard, a trackball, a touch panel and the like, and the display 142 may be realized by at least one display devices among various display devices, such as Liquid Crystal Display (LCD), Light Emission Display (LED), Organic Light Emission Display (OLED), Plasma Display Panel (PDP), and Cathode Ray Tube (CRT).

The user may input a control command related to operations of the CT apparatus 100, such as a command of moving the patient table 162, a command of selecting a scan mode, a command of a scan condition, and a command of displaying images, through the input unit 141.

The display 142 may display a screen configured to help the user to input a control command, a screen configured to display a control condition of the CT apparatus 100, or an image generated by the image processor 130.

The controller 150 may control entire operations of the CT apparatus 100. The controller 150 may include a table controller 151 controlling movement of the patient table 162, a scan controller 152 controlling a parameter, a scan mode and the like, all of which are related to a scan, in consideration of a target part of an object, a diagnostic purpose, and characteristics of the object, and a gantry controller 153 controlling the rotation of the gantry 103, the activation of the detector assembly 120, and the like.

The table controller 151 may control a moving distance and a moving direction of the patient table 162 so that a target part of the object 30 placed on the patient table 162 is located in the bore 105. For this, a driving control signal of the patient table 162 may be transmitted to the table assembly 160.

The scan controller 152 may perform a function of Auto Exposure Controller (AEC) automatically controlling an exposure parameter, may control a scan mode, and may control the activation of the detector assembly 120 depending on whether to acquire data from the integrative detection region or from the counting detection region.

When the scan controller 152 performs a function of AEC, the scan controller 152 may control an exposure parameter, such as the tube voltage, the tube current, the exposure time, a type and a thickness of the filter, a target material of anode, focal spot size, and the like, all of which are applied to the X-ray source 111. For this, Pre-shot or Scout scanning may be performed by using X-rays having low dose, and the exposure parameter may be determined by the acquired data.

The scan controller 152 controls the scan mode, the scan controller 152 may control a thickness of a slice or the number of slice acquired at one time scanning, and when multi slices are acquired, the scan controller 152 may determine whether to use the integrative detection region or the counting detection region to acquire each slice or may control the activation of each detection region depending on the result of determination.

In addition, the scan controller 152 may selectively activate the counting detection region or the integrative detection region according to whether to apply multi-energy X-rays imaging method.

The scan controller 152 may perform the controlling by itself or by a command from a user.

The gantry controller 153 may control the number of rotation and the rotation speed of the gantry 103 by transmitting a control signal to a gantry motor 107 configured to supply rotating force to the gantry 103.

Figure 3:
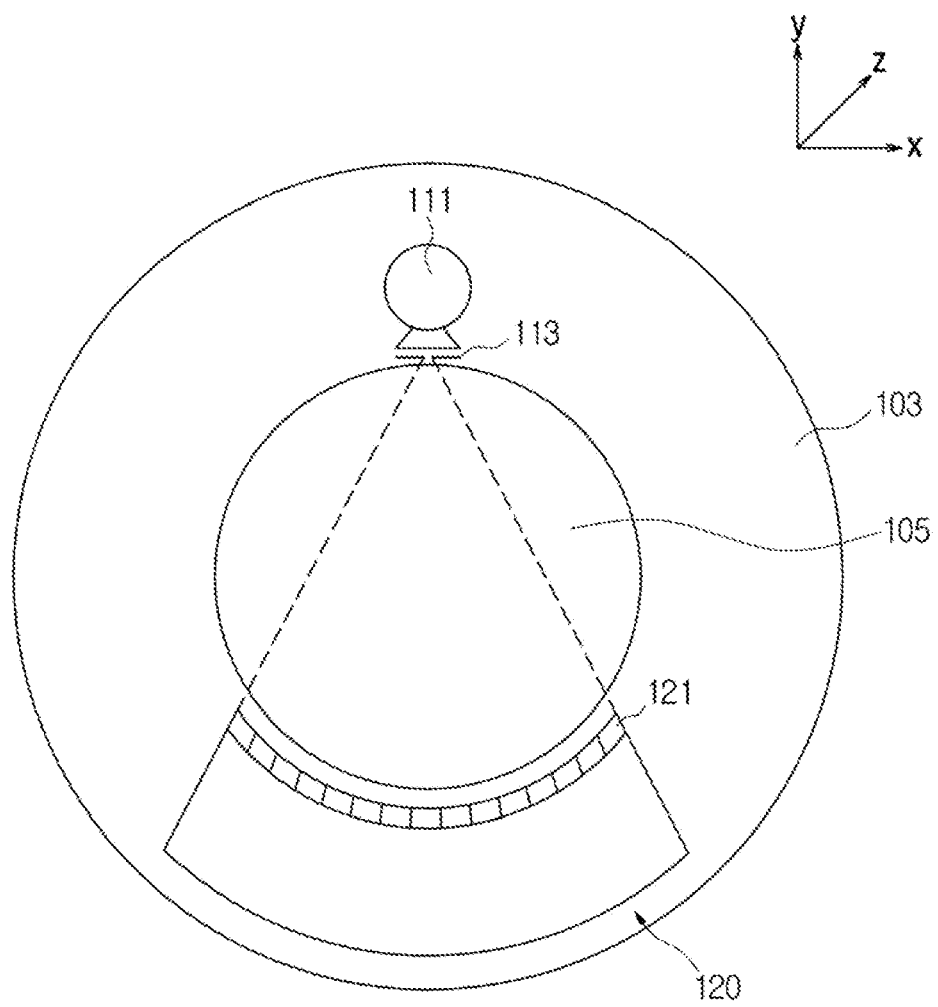
FIG. 3 is a transverse sectional view illustrating a gantry of a CT apparatus according to an exemplary embodiment.
Figure 4:
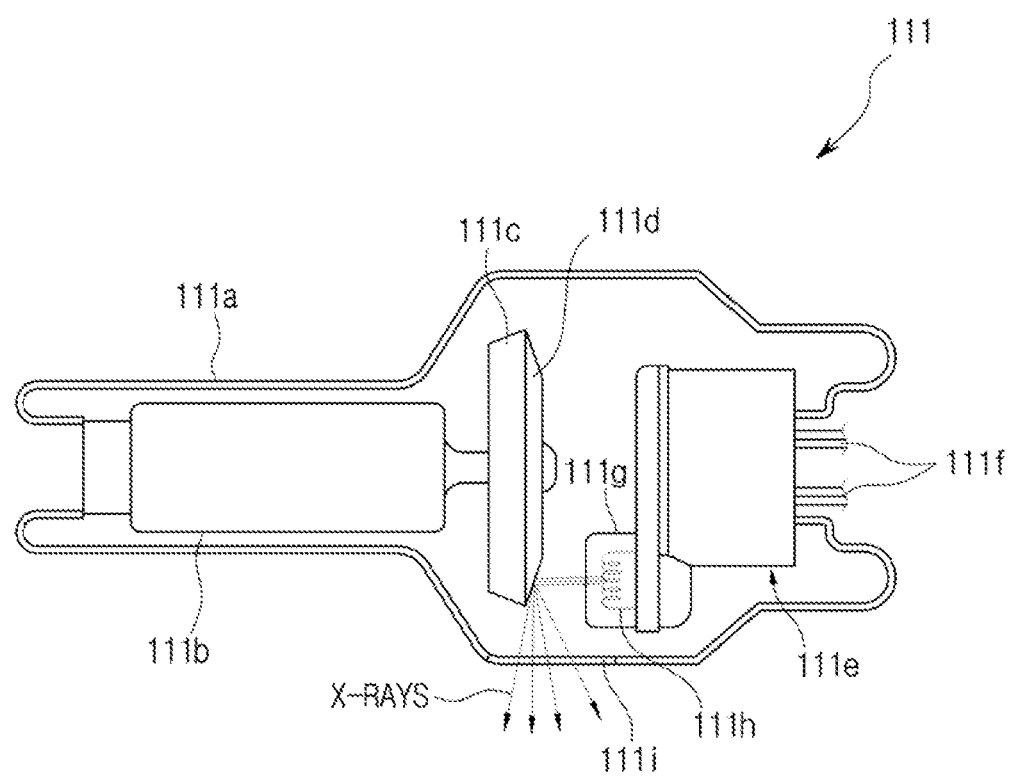
FIG. 4 is a cross-sectional view illustrating an internal configuration of an X-ray source.

FIG. 3 is a transverse sectional view illustrating a gantry of a CT apparatus according to an exemplary embodiment, and FIG. 4 is a cross-sectional view illustrating an internal configuration of an x-ray source.

Referring to FIG. 3, the X-ray source 111 and the detector assembly 120 are mounted to face each other inside the gantry 103 and rotated with 360 degree with respect to the bore 105.

A collimator 113 may be disposed in front of an X-ray incident direction of the X-ray source 111, and thus the collimator 113 may adjust a width X-ray beam emitted from the X-ray source 111. Therefore, the collimator 113 reduces scattered rays in other directions to reduce a dose of the object.

Although not shown the drawings, a collimator is disposed on a front surface of the detector assembly 120 so that X-rays may be detected in only region of interest. The collimator disposed on the front surface of the detector assembly 120 may remove scattered rays and may determine a thickness of a slice by adjusting a width of X-ray beam passed through the object 30.

The X-ray source 111 may be referred to as X-ray tube, and may generate X-rays by receiving power from the outside power supplier (not shown).

Referring to FIG. 4, the X-ray tube 111 may be realized by a diode including an anode 111$c$ and a cathode 111$e$. The cathode 111$e$ includes a filament 111$h$ and a focusing electrode 111$g$ focusing electrons. The focusing electrode 111$g$ is also referred to as a focusing cup.

The inside of the glass tube 111$a$ is maintained in a high vacuum state, such as approximately 10 mmHg, and thermoelectrons are generated by heating the filament 111$h$ of the cathode 111$e$. The filament 111$h$ may employ a tungsten filament, and the filament 111$h$ may be heated by applying a current to an electrical conductor 111$f$ connected to the filament.

The anode 111$c$ is mainly formed of copper, and a target material 111$d$ is applied or disposed on a side facing the cathode 111$e$, wherein high-resistance materials such as Cr, Fe, Co, Ni, W, and Mo may be used as the target material 111$d$. The target material is inclined at a certain angle, and as the inclined angle is increased, the focal spot size is smaller. In addition, the focal spot size is variable according to the tube voltage, the tube current, the filament size, a focused electrode size, and a distance between the anode and cathode.

When a high voltage is applied between the anode 111$c$ and the cathode 111$e$, thermoelectrons are accelerated and collide with a target material 111$g$ of the anode 111$c$, and thereby X-rays are generated. The generated X-rays are radiated to the outside through a window 111$i$, and a beryllium (Be) film may be used as a material of the window.

At this time, a filter is disposed on a front surface or a rear surface of the window 111i so that X-rays having a certain energy band may be filtered.

The target material 111d may be rotated by a rotor 111b, and when the target material 111d is rotated, a heat accumulation rate per area may be increased by 10 times in comparison with when the target material 111d is fixed, and a focal spot size may be reduced.

The voltage applied between the anode 111c and the cathode 111e is referred to as a tube voltage and a level thereof may be indicated as peak kilovoltage (kVp). As the tube voltage increases, a rate of thermoelectrons increases. As a result, X-ray energy (photon energy) generated by colliding with the target material 111d increases.

A current flowing in the X-ray tube 111 is referred to as a tube current and may be indicated as an average mA. As the tube current increases, the X-ray dose (the number of X-ray photons) increases. As a result, an X-ray dose (the number of photons of X-ray) generated by colliding with the target material 111d increases.

Therefore, the energy of the X-rays may be controlled by the tube voltage, and the intensity of X-rays or the X-ray dose may be controlled by the tube current and an X-ray exposure time. The energy of the X-rays, the intensity of X-rays or the X-ray dose may be determined according to characteristics of an object, such as a type and a thickness, or a diagnostic purpose, and the like.

The X-ray source 111 may emit monochromatic X-rays, or polychromatic X-rays. When the X-ray source 111 emits polychromatic X-rays having a certain energy band, energy band of the emitted X-rays may be defined by the upper limit and the lower limit.

The upper limit of the energy band, that is the maximum energy of the emitted X-rays, may be adjusted by a size of the tub voltage, and the lower limit of the energy band, that is the minimum energy of the emitted X-rays, may be adjusted by a filter disposed on an incident direction of the X-ray.

A filter may play a role of penetrating or filtering X-rays having a certain energy band. Therefore, a filter configured to filter X-rays having a certain band may be disposed on the front surface or rear surface of the window 111i to filter X-rays having a certain energy band.

For example, a filter formed of aluminum or copper is disposed so that X-rays having a low energy band reducing an image quality is filtered. Therefore, X-ray beam quality is hardened so that the lower limit of the energy band may be increased and an average energy of the emitted X-rays may be increased. An exposure dose of the object may be reduced.

A bowtie filter 115 (refer to FIG. 16), which will be described later, may play a role as the filter or an additional filter playing the role may be provided other than the bowtie filter 115.

Referring to FIG. 3 again, a transverse section of the detector assembly 120 has an arch shape. A detector 121 configured to convert into an electronic signal by detecting X-rays is provided on the uppermost portion of the detector assembly 120.

The detector 121 may be formed by a plurality of detector elements, and each detector element may be a pixel of the detector 121.

The detector element is classified by a method of converting detected X-rays into an electrical signal and a method of acquiring an electrical signal. According to the method of converting detected X-rays into an electrical signal, the detector element is classified by a direct conversion and an indirect conversion.

According to the method of acquiring an electrical signal, the detector element is classified by a charge integration method in which a signal is acquired from the charge after an electric charge is stored during a certain period time, and a photon counting method of counting whenever a signal is generated by a single X-ray photon.

According to the direct conversion method, when X-rays are irradiated, electron-hole pairs are temporarily generated inside a light receiving element included in the detector element, electrons move to the anode and holes move to the cathode due to an electric field applied to both ends of the light receiving element, and the detector element converts the movement into an electrical signal. In the direct conversion method, amorphous selenium (a-Se), CdZnTe, HgI2, and PbI2 may be used as the light receiving element.

According to the indirect conversion method, a scintillator is provided in an upper portion of the detector element. When X-rays irradiated from the X-ray source react with the scintillator and emit photons having visible light wavelength region, the light receiving element may detect the photons and convert into an electrical signal. In the indirect conversion method, amorphous silicon (a-Si) may be used as the light receiving element, and a thin-film GADOX scintillator, or a micro columnar or needle-shaped CSI (T1) scintillator may be used as the scintillator.

The detector 121 may employ a proper method between the direct conversion method and the indirect conversion method, or may employ different methods corresponding to a region of the detector 121, described later. For example, the indirect conversion method may be applied the integrative detection region, and the direct conversion method may be applied to the counting detection region.

When the photon counting method of the method of acquiring electrical signal is applied, the inside of an object may be imaged by using small dose, and an image having an excellent signal to noise ratio may be acquired.

In comparison with the photon counting method, in the charge integration method, X-ray flux detected by the detector 121 is higher. That is, saturation level is higher and dynamic range is larger.

Therefore, when applying the photon counting method and the charge integration method to the detector 121 by properly combing those methods, performance of the detector 121 may be improved, and it may be helpful to generate a diagnostic imaging appropriate for various purposes.

In the CT apparatus 100 according an exemplary embodiment, the detector 121 is configured by combining the photon counting method and the charge integration method. Hereinafter a detailed configuration and a structure of the detector 121 will be described.

Figure 5:
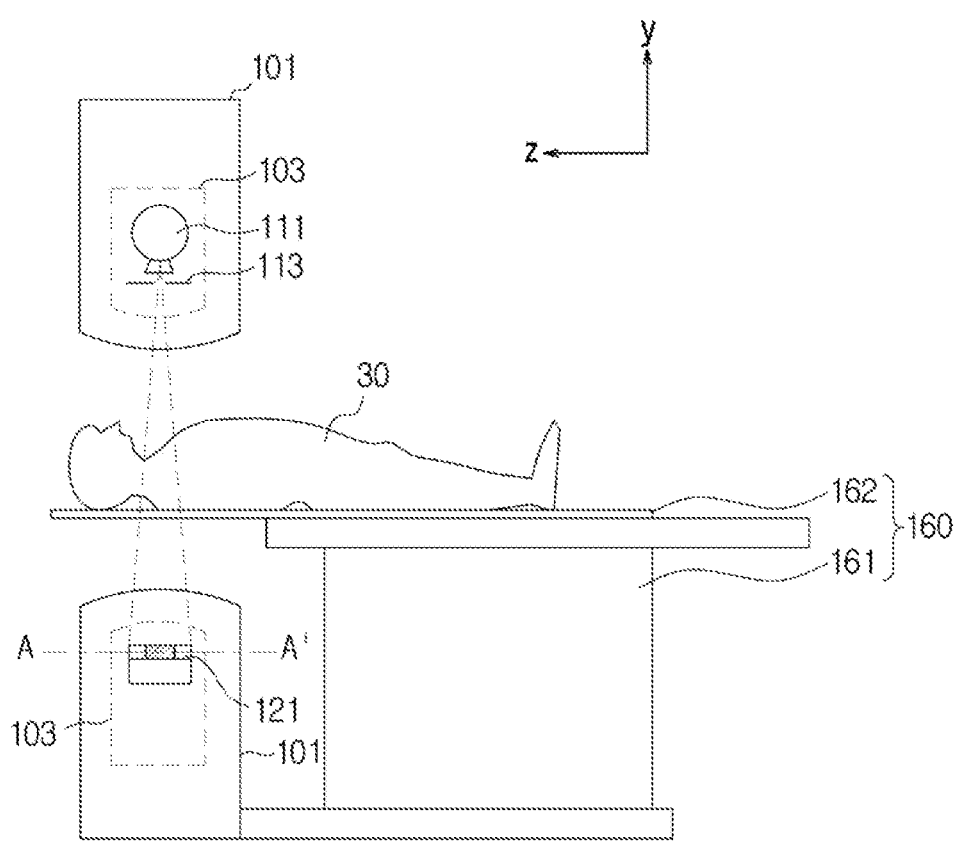
FIG. 5 is a longitudinal cross sectional view illustrating a gantry of a CT apparatus according to an exemplary embodiment.
Figure 6:
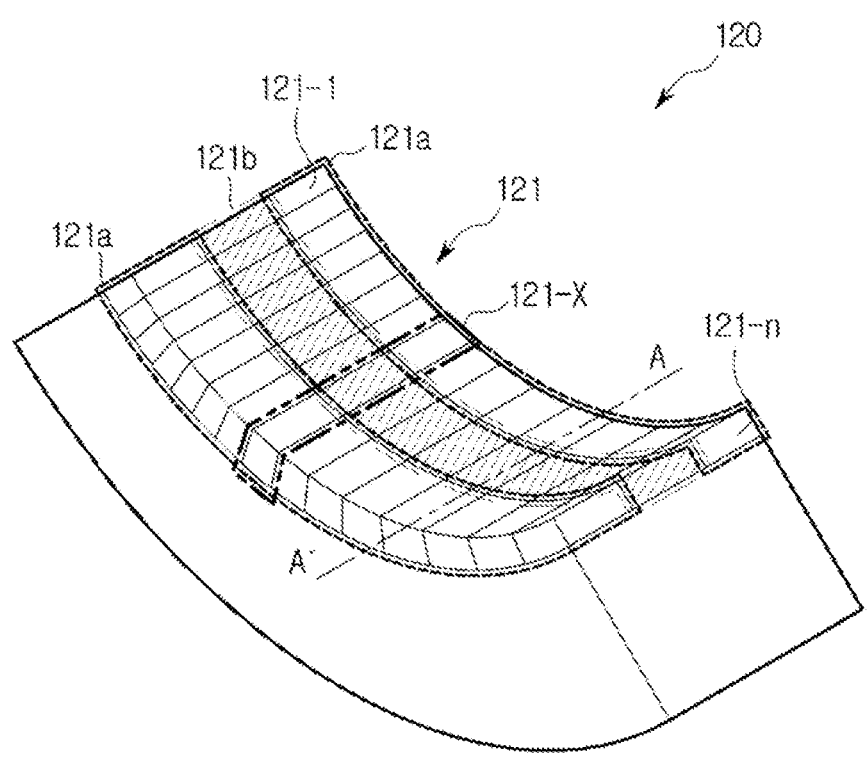
FIG. 6 is a perspective view illustrating an exemplary detector assembly included in a CT apparatus according to an exemplary embodiment.

FIG. 5 is a longitudinal cross sectional view illustrating a gantry of a CT apparatus according to an exemplary embodiment and FIG. 6 is a perspective view illustrating an exemplary detector assembly included in a CT apparatus according to an exemplary embodiment.

Referring to FIGS. 5 and 6, the center of the detector 121 with respect to a Z-axis direction may be configured by a counting detection region 121b and the remaining edge portions of the detector may be configured by an integrative detection region or regions 121a. The edge portions of the detector may refer to an inner portion and an outer portion, of the detector, with respect to an inner side 200 of the housing 101 and an outer side 202 of the housing 101 (or the gantry) in the Z-axis direction. A rotation axis of the gantry, i.e., an axis in parallel to a longitudinal axis of the object 30 may be defined as a Z-axis, an axis parallel to an upward and downward directions with respect to ground may be defined as a Y-axis, and an axis perpendicular to the Y- and Z-axes may be defined as an X-axis. The positive direction and the negative direction of each axis may be switched with respect to each other.

When charge is generated in the integrative detection region 121a on which the X-rays are incident, the generated charge may be stored during a certain period of time and then an electrical signal is acquired from the charge. That is, an electrical signal is acquired in the charge integration method.

In the counting detection region 121b, whenever a signal is generated by one X-ray photon, the number of photons, which generates a voltage signal having larger size than a certain size, may be counted by comparing the generated signal size with a threshold voltage. That is, according to the counting photon method, an electrical signal is acquired. Hereinafter, an electrical signal acquired in the integrative detection region 121a and the counting detection region 121b or a signal which is the electrical signal is converted into a digital form may be referred to as X-ray data.

Data having an excellent signal to noise ratio (SNR) may be acquired by using low dose through the counting detection region 121b formed in the central portion of the detector 121, and data having high dynamic range may be acquired through the integrative detection region 121a formed in an inner and outer portion of the detector 121.

The detector 121 may have a structure in which a plurality of detection modules 121-1 through 121-n is arranged in one dimensional (1D) array. Hereinafter a structure of a single detection module will be described by using any single detection module 121-x (x is a random integer between 1 and n) among the plurality of detection modules 121-1 through 121-n.

Figure 7:
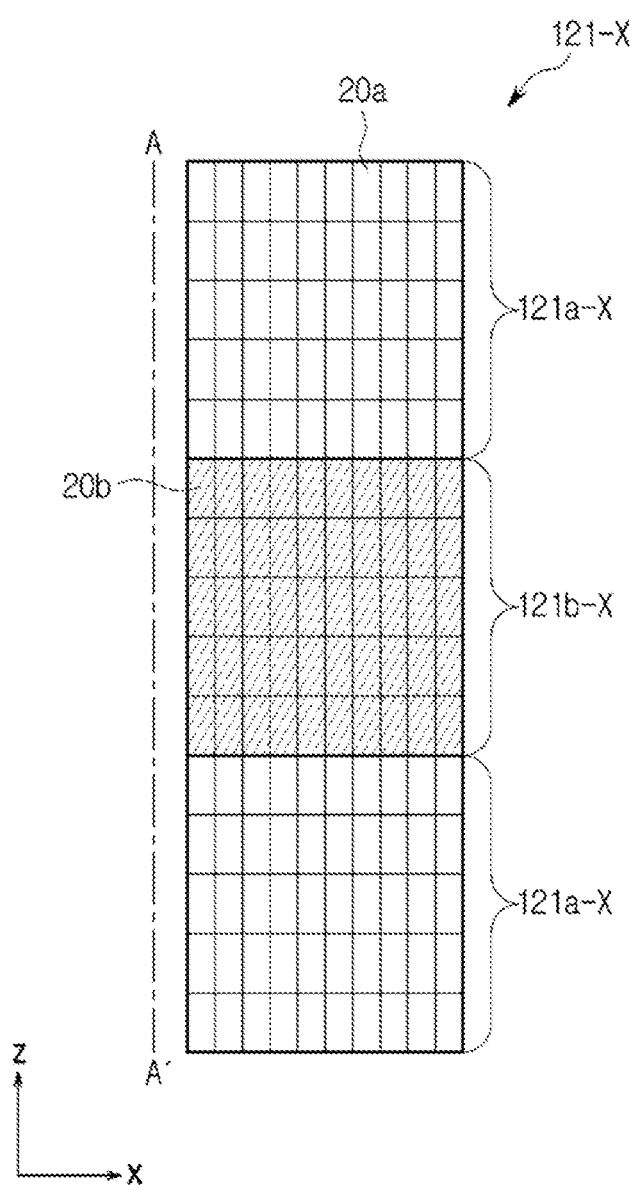
FIG. 7 is a plane view from above of a single detection module.

Referring to FIG. 7, in the single detection module 121-x, a counting detection region 121b-x may be formed in the center with respect to a A'-A direction, and an integrative detection region 121a-x may be formed on inner and outer portions of a counting detection region 121b-x, with respect to a A'-A direction. The A'-A direction may represent the same direction as the Z-axis direction of the gantry 103.

The counting detection region 121b-x may be configured by counting detector elements 20b arranged in a 2D matrix, and the integrative detection regions 121a-x may be configured by integrative detector elements 20a arranged in 2D matrices.

The integrative detector elements 20a constituting the integrative detection region 121a-x may include a light receiving element converting a charge flow by detecting X-rays or visible rays, and a capacitor storing a charge flow, and may further include additional components, such as an amplifier amplifying an electrical signal size formed by a charge flow, as needed.

Figure 8:
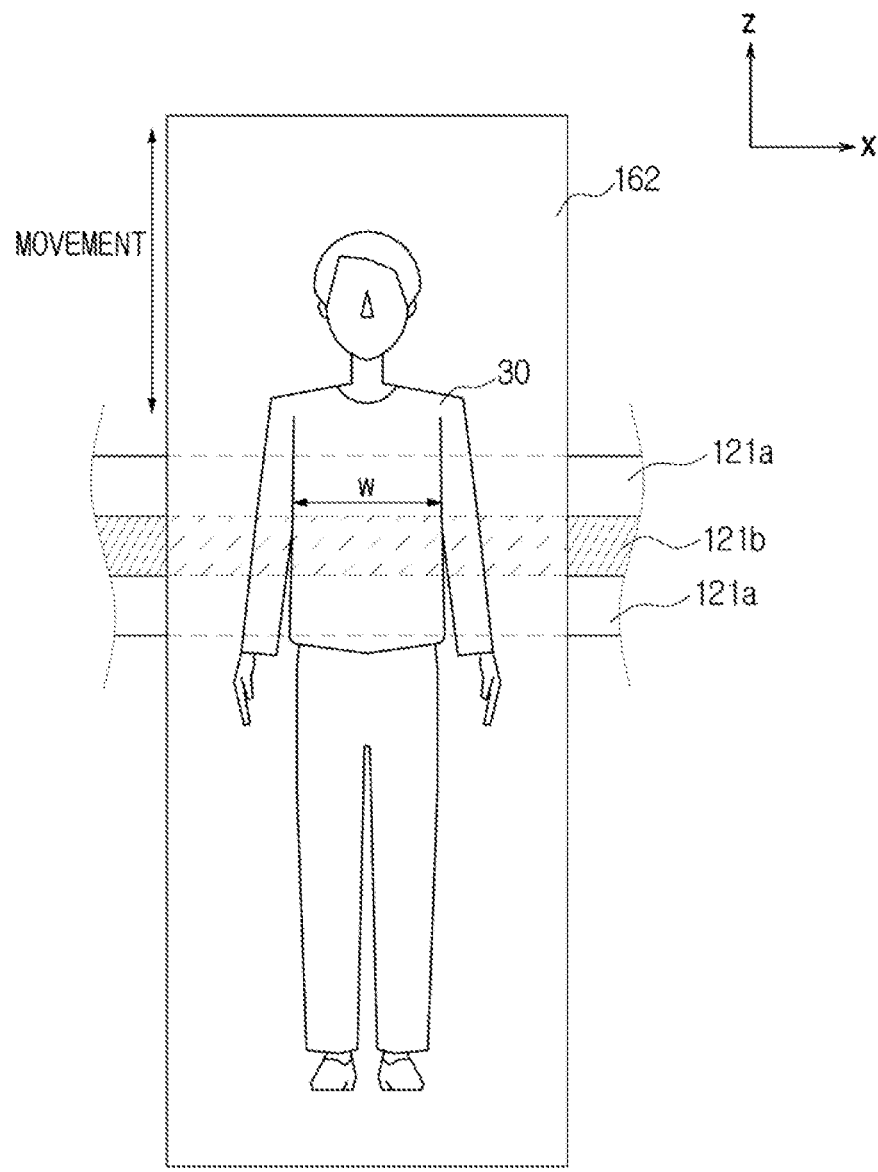
FIG. 8 is a view illustrating a relation between a detector position and an object position.

FIG. 8 is a view from above of the object 30 in a case where the object 30 placed on the patient table 162 is transferred to the bore 105 to be placed on an upper portion of the detector assembly 120.

As illustrated in FIG. 8, when the detector 121 is configured in a way that the integrative detection region 121a, the counting detection region 121b and the integrative detection region 121a are arranged in this order in the Z-axis direction, the counting detection region 121b may cover all of the region of interest even though a width of the region of interest is large.

In addition, since scanning is performed while the patient table 162 is moved in the Z-axis direction, there may be no problem to acquire a signal about entire region of interest even when a length of the region of interest is longer than a length of the counting detection region 121b. That is, according to a structure of the detector assembly 120 of the CT apparatus 100 in accordance with an exemplary embodiment, desired scanning may be performed regardless of the size of an object or a region of interest.

The counting detector elements 20b constituting the counting detection region 121b-x may count the number of photons according to the size of generated electrical signal, and hereinafter a description thereof will be described with a structure of FIG. 9 as an example.

Figure 9:
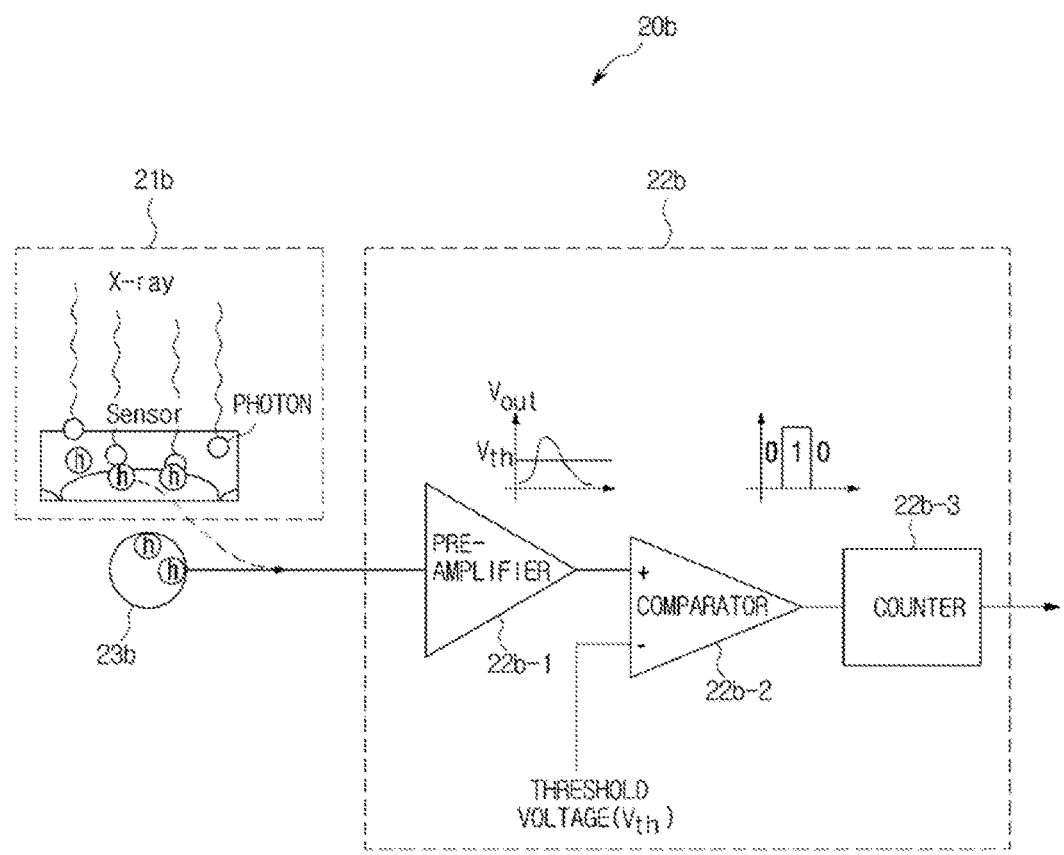
FIG. 9 is a view illustrating a structure of a detector element constituting a counting detection region.

FIG. 9 is a view illustrating a structure of a detector element constituting a counting detection region.

Referring to FIG. 9, one or more of the counting detector elements 20b may include a light-receiving element 21b converting X-rays into a charge flow and a readout circuit 22b reading the charge flow and counting the number of photons.

The light-receiving element 21b and the read out circuit 22b may be coupled to each other in a flip chip bonding method, particularly may be coupled to each other in such a way of forming bump 23b such as solder (PbSn), indium (In), reflowing and pressuring the bump 23b by applying heat.

When photons of the X-ray is incident on the light-receiving element 21b, electrons in valence band receive an energy of the photons and then pass over an energy difference of band gap, thereby being excited to conduction band. Therefore, electron-hole pairs are generated in the depletion region.

When metal electrodes are generated on each p-type layer and n-type substrate of the light receiving elements 21b, and reverse bias is applied, an electron among electron-hole pairs generated in the depletion region is dragged to an n-type region, and a hole is dragged to a p-type region. The hole dragged to the p-type region is inputted to the read out circuit 22b through the bump bonding 23b to allow an electrical signal generated by a photon to be read. However, according to a structure of the light receiving element 21a and the applied voltage, an electron may be inputted to the read out circuit 22b.

When a charge is inputted to the read out circuit 22b, a pre-amplifier 22b-1 of the read out circuit 22b performs charging an input charge generated from a single photon and outputs a voltage signal corresponding to the input charge.

The voltage signal outputted from the pre-amplifier 22b-1 is transferred to a comparator 22b-2, which outputs a pulse signal of 1 or 0 according to the result of comparing a random threshold voltage Vth with the inputted voltage signal. A counter 22b-3 outputs a counting signal, i.e., X-ray data by counting the number of times of appearing '1'.

Therefore, a signal outputted from the counting detector element 20b includes information related to the number of photons having larger energy than a certain reference level.

Referring to FIGS. 6, 7, and 9 again, the counting detection region 121b-x of the single detection module 121-x may be formed by a plurality of counting detector elements 20b, and the counting detection region 121b of the entire detector 121 may be formed by n counting detection regions included in N detection modules 121-1 through 121-n.

In addition, the integrative detection region 121a-x of the single detection module 121-x may be formed by a plurality of counting detector elements 20a, and the integrative detection region 121a of the entire detector 121 may be formed by n integrative detection regions included in N detection modules 121-1 through 121-n.

Multi-energy X-ray imaging method may be used to improve contrast between tissues constituting the object 30. According to the multi-energy X-ray imaging method, an X-ray signal about the object 30 is acquired in a plurality of energy bands, which are different from each other, and an image separated according to characteristics of tissue constituting the object 30 may be acquired by processing X-ray signals acquired in the plurality of energy bands.

To apply the multi-energy X-ray imaging method, an X-ray having a desired energy band may be respectively emitted from an X-ray source, or an X-ray having a band including all of desired energy band may be emitted from the X-ray source and a detector may detect the X-ray to separate the X-ray into a desired energy band.

According to the CT apparatus 100 in accordance with an exemplary embodiment, the counting detection region 121b is included in the detector 121 and thus the latter method may be used.

Figure 10:
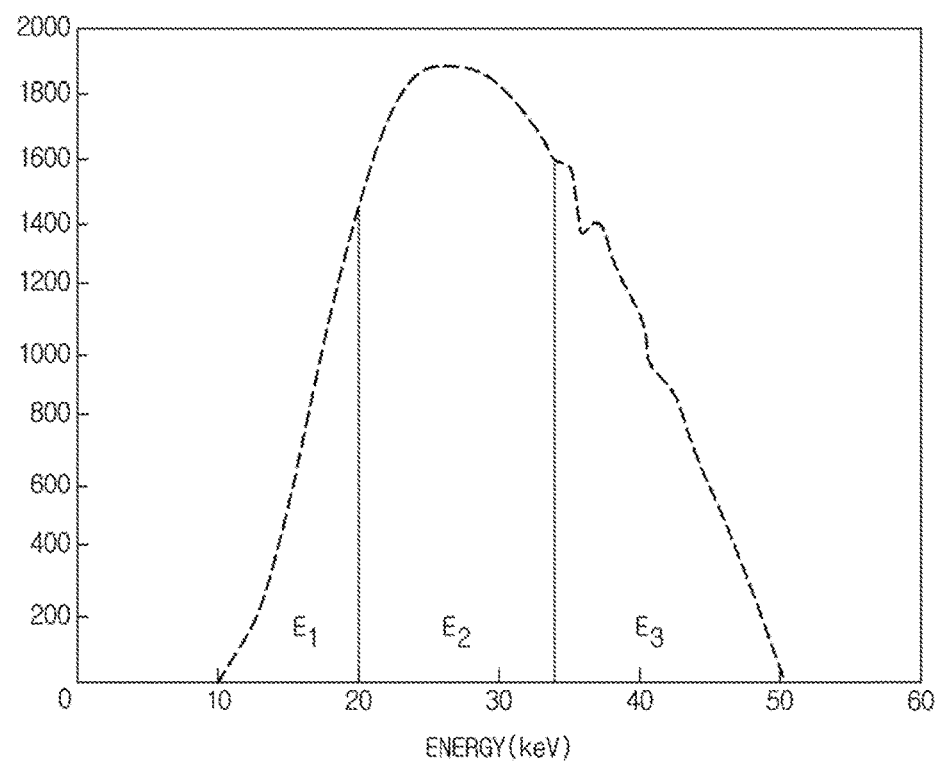
FIG. 10 is a view illustrating an energy spectrum of an X-ray irradiated from an X-ray source.
Figure 11:
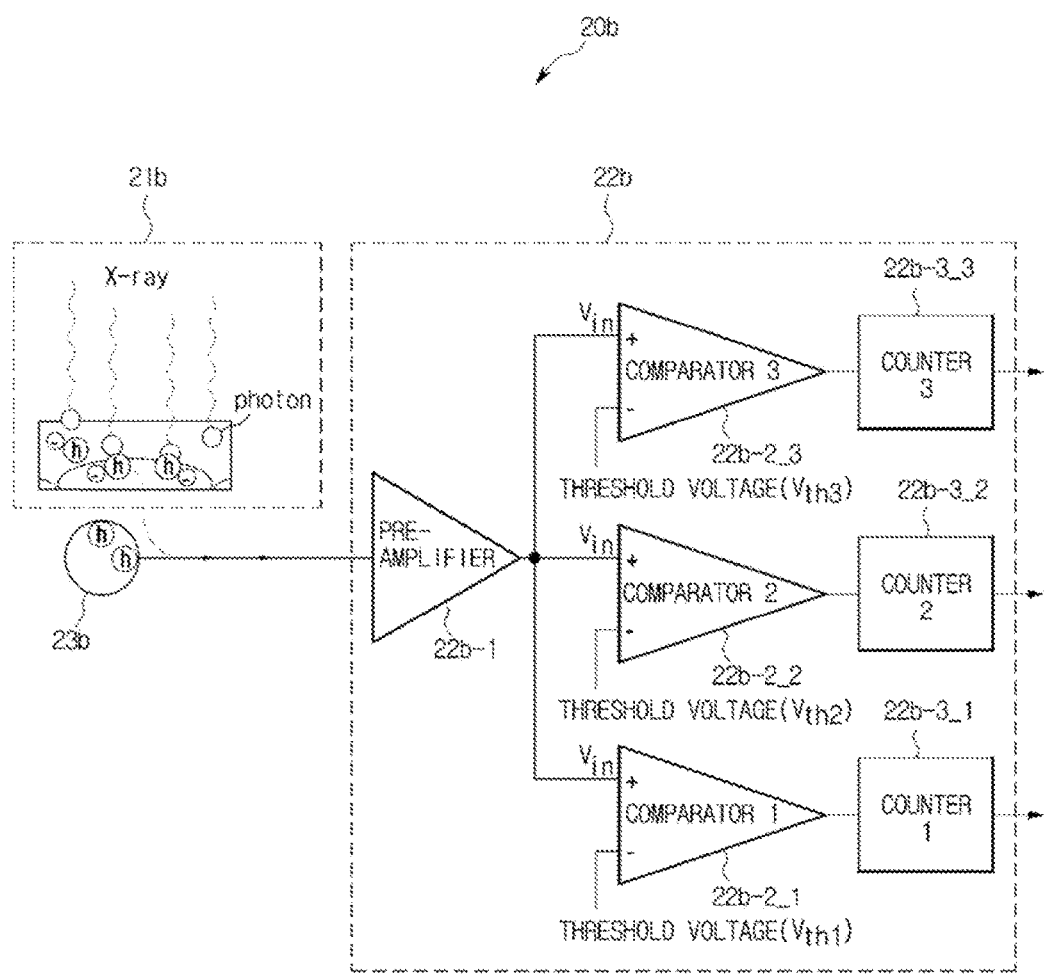
FIG. 11 is a view illustrating a structure of a detector element capable of dividing X-ray signals into three energy bends.

FIG. 10 is a view illustrating an energy spectrum of an X-ray irradiated from an X-ray source and FIG. 11 is a view illustrating a structure of a detector element capable of dividing X-ray signals into three energy bends.

For example, to acquire an X-ray signal corresponding to three energy bands $E_1$, $E_2$, $E_3$ different from each other, the X-ray source 111 may generate and emit an X-ray having a band including all of energy bands $E_1$, $E_2$, $E_3$, as illustrated in FIG. 10. Particularly, an X-ray in which 10 keV, which is a lower limit of the lowest energy band $E_1$, is set to a lower limit, and 50 keV, which is an upper limit of the uppermost energy band $E_3$, is set to an upper limit, may be emitted. For this, in a state where a tube voltage of the X-ray source is set to be 50 kVp, an X-ray may be generated and an X-ray having a band of 0-10 keV may be filtered.

The counting detection region 121b of the detector 121 may detect an X-ray emitted from the X-ray source to separate the X-ray into three energy bands. For this, the counting detector element 20b has a structure configured to separate an electrical signal generated by X-rays according to three energy bands.

As illustrated in FIG. 11, when an electrons or an hole generated in the light receiving element 21b by a single photon is outputted as a voltage signal through the bump bonding 23b and the pre amplifier 22b-1 of the read out circuit 22b connected to the light receiving element 21b, the voltage signal $V_{in}$ is inputted to three comparators 22b-2_1, 22b-2_2, 22b-2_3.

A threshold voltage corresponding to an energy band intended to be separated is inputted to each comparator. Since a size of generated voltage signal is different according to energy what an incident photon has, a size of voltage corresponding to a lower energy of an energy band intended to be separated may be estimated to be inputted as the threshold voltage to each comparator.

A threshold voltage ($V_{th1}$) corresponding to a lower limit of a first energy band $E_1$ may be inputted to a first comparator 22b-2_1, a threshold voltage ($V_{th2}$) corresponding to a lower limit of a second energy band $E_2$ may be inputted to a second comparator 22b-2_2, and a threshold voltage ($V_{th3}$) corresponding to a lower limit of a third energy band $E_3$ may be inputted to a third comparator 22b-2_3.

When the first comparator 22b-2_1 compares the threshold voltage ($V_{th1}$) with an input voltage $V_{in}$ and the input voltage $V_{in}$ is larger than the threshold voltage ($V_{th1}$), the first comparator 22b-2_1 may output a pulse of '1' representing a state of 'high', and when the input voltage $V_{in}$ is less than the threshold voltage ($V_{th1}$), the first comparator 22b-2_1 may output a pulse of '0' representing a state of 'low'.

A first counter 22b-3_1 receives a pulse signal outputted from the first comparator 22b-2_1 and counts the number of times of outputting '1' in the first comparator 22b-2_1. A count value of the first counter 22b-3_1 becomes the number of photons generating larger voltage than the threshold voltage ($V_{th1}$) that is the number of photons having larger energy than the lower limit of the first energy band.

Similarly, the second counter 22b-3_2 counts the number of photons generating larger voltage than the threshold voltage ($V_{th2}$) and the third counter 22b-3_3 counts the number of photons generating larger voltage than the threshold voltage ($V_{th3}$).

FIGS. 10 and 11 are examples applied to the CT apparatus 100 according to an exemplary embodiment, but the number and a range of energy bands may be adjusted according to the diagnostic purpose or characteristics of an object.

The structure of FIGS. 6 and 7 is an example of the CT apparatus 100, but the CT apparatus may have various structures.

Figure 12:
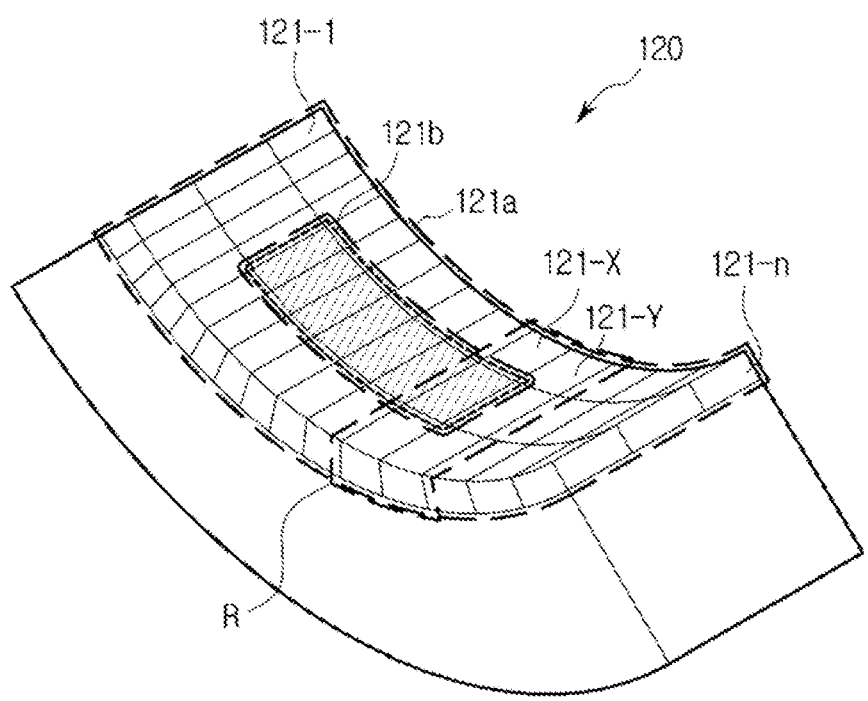
FIG. 12 is a perspective view illustrating another exemplary detector assembly included in a CT apparatus according to an exemplary embodiment.
Figure 13:
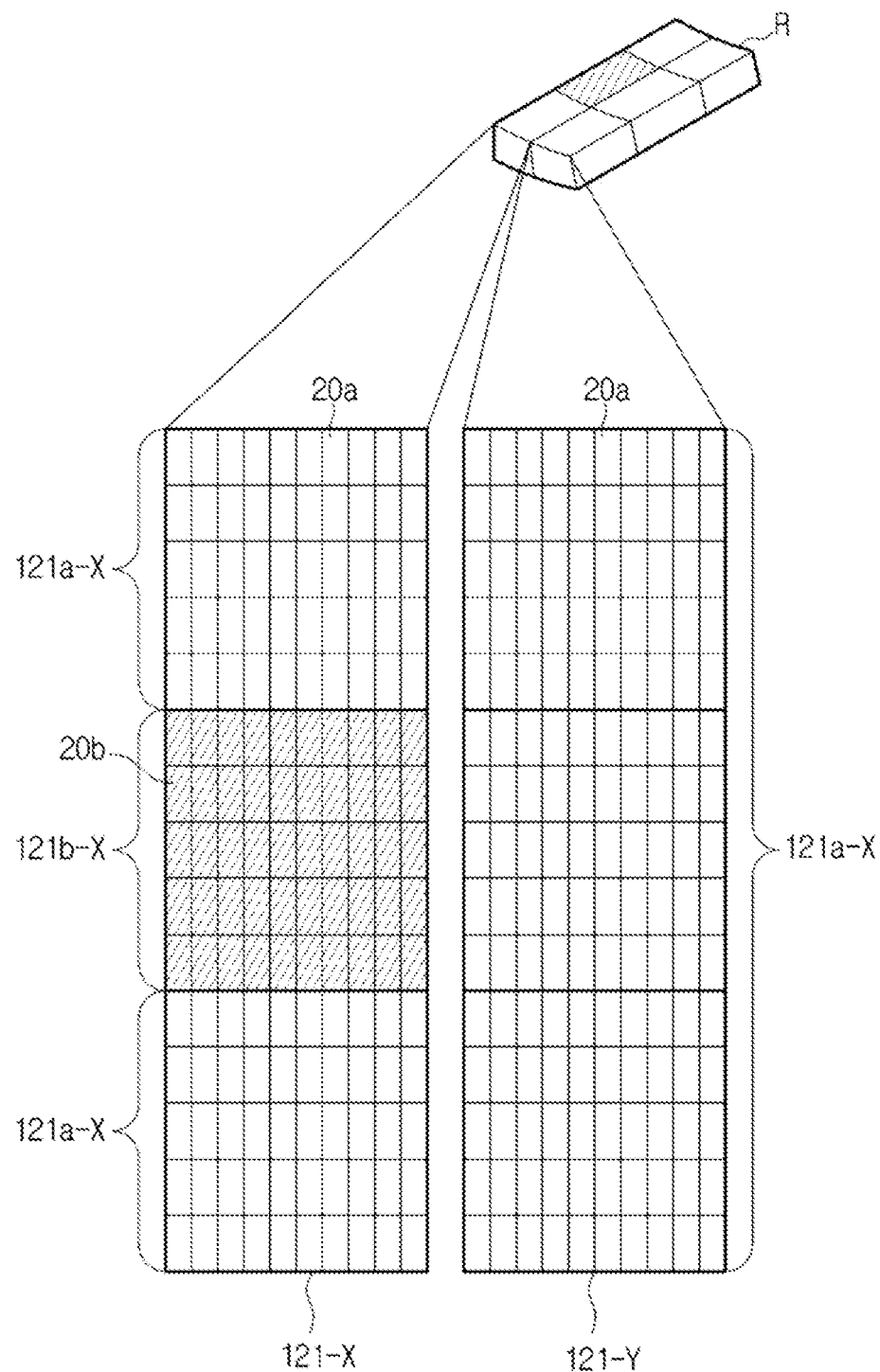
FIG. 13 is a plane view from above of a structure of a detection module included in a detector assembly of FIG. 12.

FIG. 12 is a perspective view illustrating another exemplary detector assembly included in a CT apparatus according to an exemplary embodiment and FIG. 13 is a plane view from above of a structure of a detection module included in a detector assembly of FIG. 12.

As illustrated in FIG. 12, a detector assembly 120 in accordance with another embodiment of the present disclosure may be formed in a way that a counting detection region 121b forms the central portion of a detector 121 and an integrative detection region 121a forms an edge portion surrounding the counting detection region 121b. An image having an excellent signal to noise ratio (SNR) may be acquired by using a low dose through the counting detection region 121b formed in the central portion of the detector 121, and an image having high dynamic range may be acquired through the integrative detection region 121a formed in the edge portion of the detector 121.

In addition, when a CT image is imaged, a region of interest may be mainly placed in the counting detection region 121b, and a background region may be placed in the integrative detection region 121a. Therefore, as for the region of interest, an image having an excellent signal to noise ratio (SNR) may be acquired with a low dose by using the counting detection region 121b, and as for the background region, a saturation phenomenon may be reduced by using the integrative detection region 121a.

As above-described embodiment, a detector 121 according to an exemplary embodiment may have a structure in which a plurality of detection modules 121-1 through 121-n is arranged in 1D array. Hereinafter, a single detection module will be described by using detection modules 121-x, 121-y both of which are adjacent to each other and placed in a region R, among the plurality of detection modules 121-1 through 121-n.

Referring to FIG. 13, in a detection module 121-x, a counting detection region 121b-x may be formed in the center with respect to a Z-axis and an X-axis, and an integrative detection region or regions 121a-x may be formed in an inner and outer portion of the counting detection region 121b-x, with respect to the inner side 200 and the outer side 202 of the housing of the gantry.

The counting detection region 121b-x may be configured by counting detector elements 20b arranged in a 2D array, and the integrative detection regions 121a-x may be configured by integrative detector elements 20a arranged in a 2D array.

The detection module 121-y may be configured by only the integrative detection region 121a-x, and, as a result, may be configured by only the integrative detector elements 20a.

Therefore, a portion of the detection module 121-x may be included in the counting detection region 121b of the entire detector 121, and another portion may be included in the integrative detection region 121a. Meanwhile, all the detection modules 121-y may be included in the integrative detection region 121a of the entire detector 121.

As described above, a signal acquired in the integrative detection region 121a and a signal acquired in the counting detection region 121b are transferred to the image processor 130 as digital X-ray data, and the image processor 130 reconstructs a CT image of the object 30 by using the transferred data.

Figure 14:
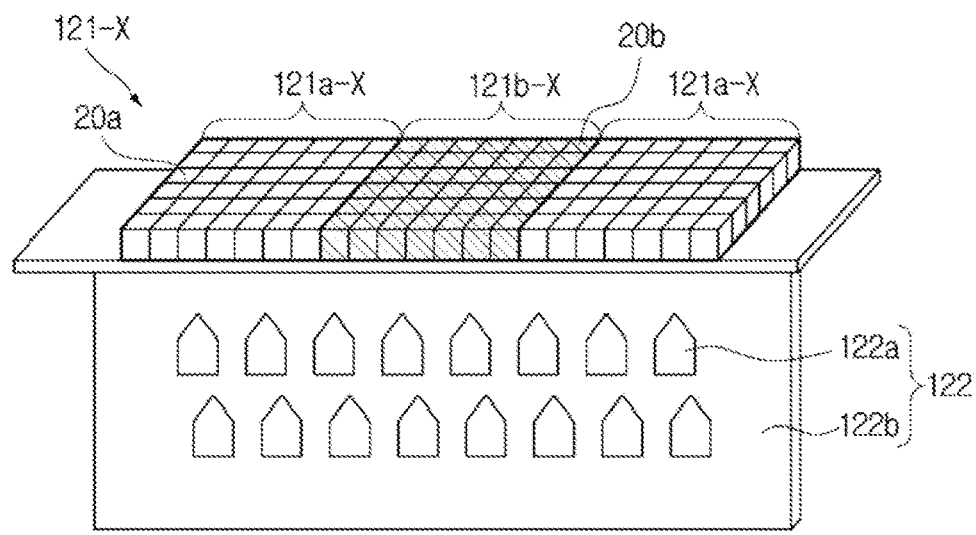
FIG. 14 is a view illustrating a data obtainer connected to a single detection module.
Figure 15:
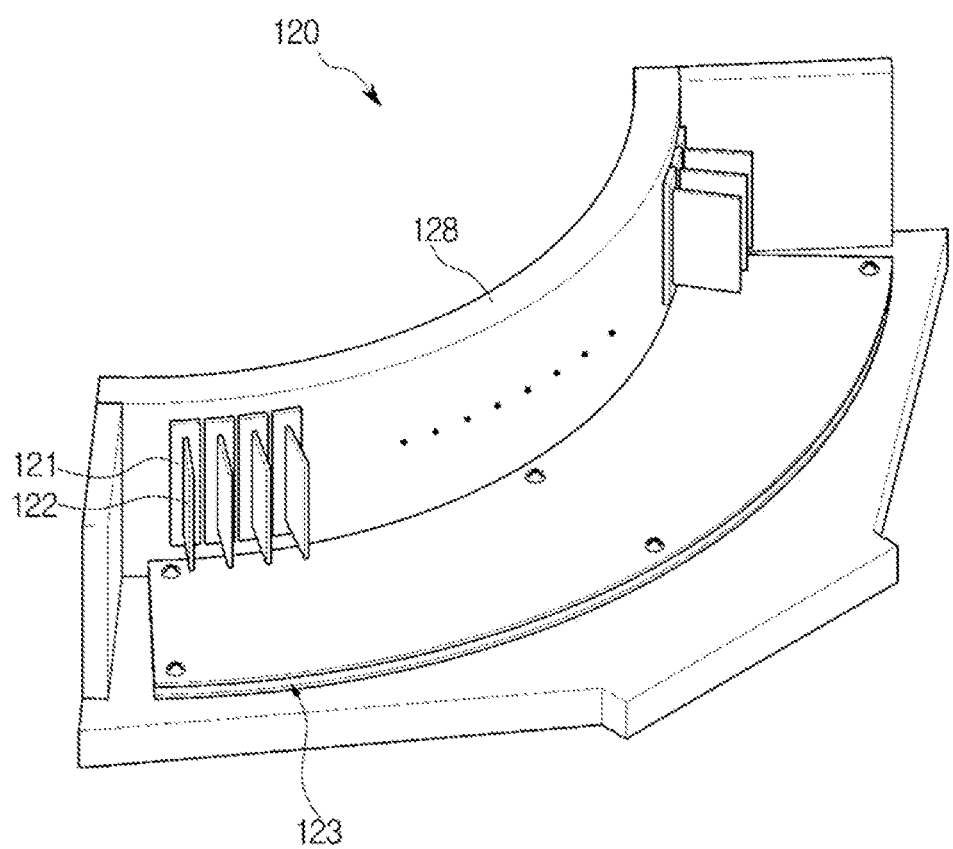
FIG. 15 is an exploded view illustrating an internal structure of a detector assembly to which a plurality of detection modules is mounted.

FIG. 14 is a view illustrating a data obtainer connected to a single detection module and FIG. 15 is a view illustrating an internal structure of a detector assembly to which a plurality of detection modules is mounted.

Referring to FIG. 14, a data obtainer 122 may be connected to a lower portion of the single detection module 121-x including the plurality of detector elements 20a and 20b, and the data obtainer 122 may be provided for the number of the detection modules n. Although not shown in the drawings, the detection module 121-x and the data obtainer 122 may be connected to each other through a flexible cable.

The data obtainer 122 includes a substrate 122b and an analog to digital converter (ADC) module 122a formed on the substrate 122b. When a signal is inputted from the detection module 121-x, the data obtainer 122 may acquire digital X-ray data in a way that the ADC module 122a converts a signal in analog form into a digital form which can be processed in the image processor 130.

The ADC module 122a may be provided with a plurality of channels so that a single ADC module 122a may convert into a digital signal by receiving a signal from a plurality of pixels of the detector 121. In this case the ADC module 122a may include analog to digital converter (ADC) and multiplexer (MUX) having a plurality of channels connected to the ADC. An electrical signal outputted from the detector elements 20a and 20b of the detection module 121-x passes through the MUX and is inputted to the ADC to be converted into digital data.

For example, a signal outputted from the detector elements 20a and 20b may be a micro signal, and thus an amplifier may be provided in an input terminal of the MUX so that a signal may be converted into a digital signal after amplifying the signal to be larger than a certain size.

Referring to FIG. 15, the detector assembly 120 may further include a data collector 123, e.g., a data acquisition board, collecting digital data acquired in the data obtainer 122, and the data collector 123 may be formed on a back plane (BP) board of a frame 128. The data collector 123 collects digital data from the data obtainer 122 and transfers the digital data to the image processor 130, and the image processor 130 reconstructs an image of an object by using the transferred digital X-ray data.

When reconstructing an image of an object by using the transferred digital X-ray data, the image processor 130 may correct the acquired data from the counting detection region 121b.

Particularly, a phenomenon, such as pile-up effect, appearing in the counting detector elements 20b may cause a distortion of X-ray data wherein the pile-up effect is that the next photon is detected before acquiring a signal corresponding to a single photon is completed, and thus a signal for two photons is recognized as a signal for a single photon.

The pile-up effect may affect response characteristics of the detector element 20b so that a section in which linearity in a relation between X-ray flux and output of the detector element 20b is secured may be reduced. Therefore the distortion of an entire image may be generated.

In comparison with the counting detector element 20b, the integrative detector element 20a has a relatively high saturation level, and a relatively wide section securing the linearity due to not being affected by the pile-up effect.

Therefore, the image processor 130 may correct data acquired from the counting detector element 20b by using data acquired from the integrative detector element 20a.

For example, when X-rays are irradiated in a state where the object 30 is not placed in an irradiation path of X-rays, i.e., the bore 105, the image processor 130 may calculate a calibration function or a calibration parameter by using a relation between X-ray data acquired by the integrative detection region 121a of the detector 121 and X-ray data acquired by the counting detection region 121b, and may correct data, which is acquired during scanning the object 30, by using the calibration function or the calibration parameter.

Figure 16:
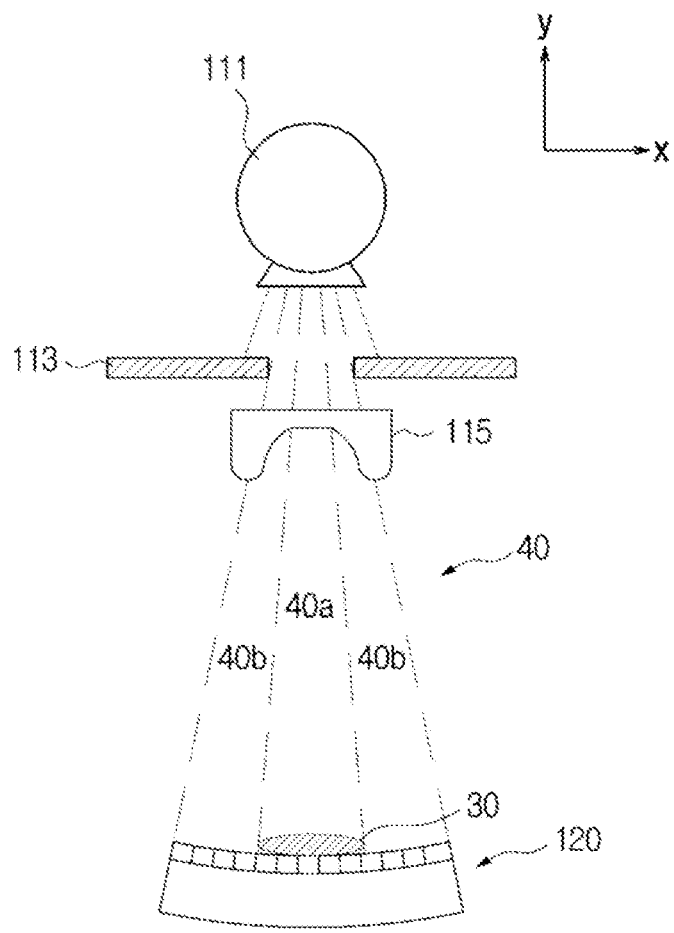
FIGS. 16 and 17 are views illustrating characteristics of X-rays incident on a detector when a bowtie filter is mounted.
Figure 17:
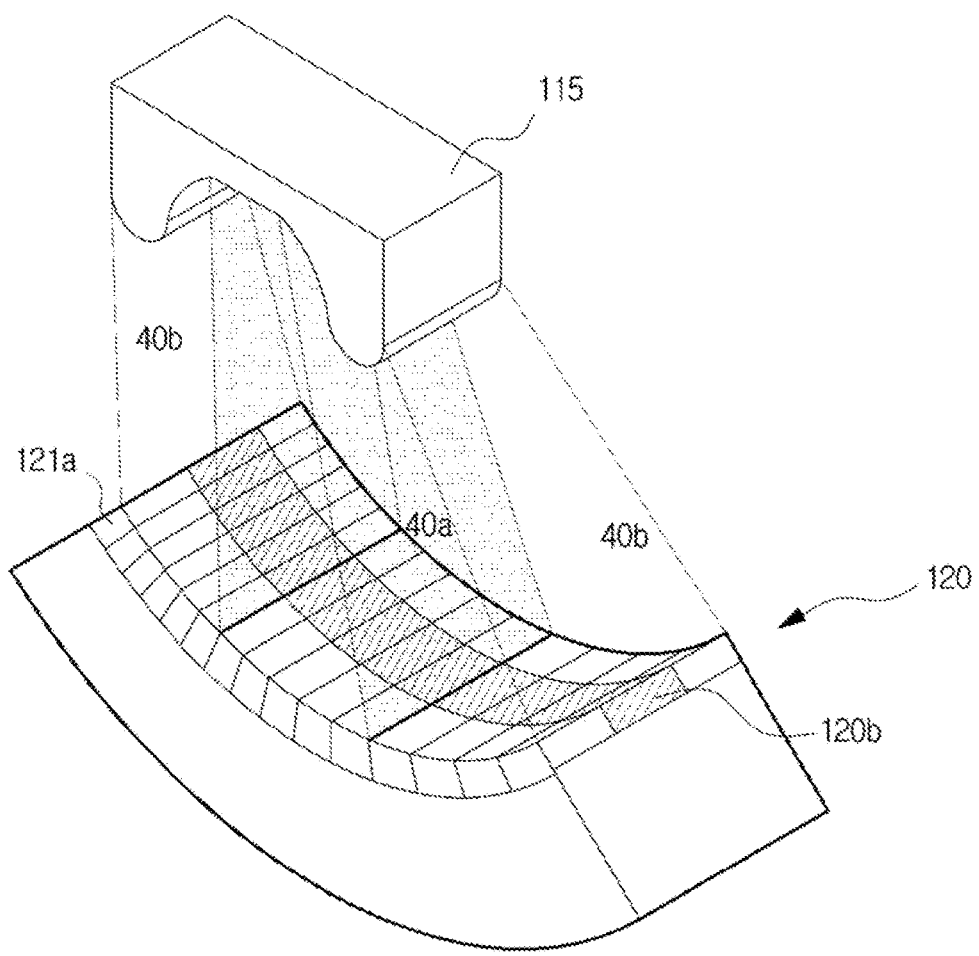

FIGS. 16 and 17 are views illustrating characteristics of X-rays incident on a detector when a bowtie filter is mounted.

When performing scan by using the CT apparatus 100 according to an exemplary embodiment, a filter having a certain shape may be mounted between the X-ray source 111 and the object 30 for X-ray beam shaping. Such a filter may be referred to as a bowtie filter.

A bowtie filter 115 may reduce entire radiation dose, particularly, may reduce a larger radiation dose of both edges than the center with respect to the X-axis direction due to a bowtie shape, as illustrated in FIGS. 16 and 17. In general, the object 30 or a region of interest is placed in the center and a background region is often placed on both edge portions with respect to the X-axis direction.

When the object 30 is not placed in the background region, the attenuation coefficient is very low or a portion having a very small thickness of the object 30 is placed, X-ray flux, which passes through the background region to be incident on the detector 121, may have a saturation level and it may cause loss and distortion of image information.

Therefore, when the bowtie filter 115 having a shape of FIGS. 16 and 17, is mounted to the irradiation path of X-rays of the X-ray source 111, it may be help to prevent the loss and distortion of image information by reducing X-ray flux incident on the background region.

The image processor 130 may correct data acquired by the counting detection region 121b by using data acquired by the integrative detection region 121a. For this, data acquired at the same conditions may be used to enhance the accuracy of calibration.

For example, when the integrative detection region 121a detects a first X-ray beam 40a passing through the edge portion, i.e., a thick portion of the bowtie filter 115 to acquire X-ray data, and the counting detection region 121b detects a second X-ray beam 40b passing through the central portion, i.e., a thin portion of the bowtie filter 115 to acquire X-ray data, the accuracy of calibration may be reduced since those data becomes outputs corresponding to inputs different from each other.

As the CT apparatus 100 according to an exemplary embodiment, when the integrative detection region 121a and the counting detection region 121b are arranged in the Z-axis direction, X-rays having the same beam quality may be incident on the integrative detection region 121a and the counting detection region 121b. That is, both of the first X-ray beam 40a and the second X-ray beam 40b are incident on the counting detection region 121b, and both of the first X-ray beam 40a and the second X-ray beam 40b are incident on the integrative detection region 121a.

Therefore, according to the CT apparatus 100 in accordance with an exemplary embodiment, X-ray beam having the same quality may be incident on the counting detection region 121b and the integrative detection region 121a by using a simple structure, and the accuracy of calibration may be enhanced by performing calibration by using X-ray data corresponding to the same beam quality.

The bowtie 115 may be formed of a plurality of material having attenuation characteristics of X-rays different from each other. For example, in the X-axis direction, both edge portions may be formed of material capable of absorbing relatively large amount of X-rays and the central portion may be formed of material capable of absorbing relatively small amount of X-rays.

A thickness of the bowtie filter 115 in the X-axis direction may be kept constant, and only material forming the filter may be configured differently in the X-axis direction, as mentioned above.

Alternatively, it may be possible to alter at least one of a configuration and a thickness of the material in the Z-axis direction. For example, a configuration and a thickness of material of a portion corresponding to the integrative detection region 121a and a configuration and a thickness of material of a portion corresponding to the counting detection region 121b may be different from each other. The portion corresponding to the integrative detection region 121a may have a smaller thickness or may be composed of material capable of absorbing relatively small amount of X-rays and the portion corresponding to the counting detection region 121b may have a larger thickness or may be composed of material capable of absorbing relatively large amount of X-rays, and vice versa. As needed, the material may be composed differently regardless of the integrative detection region or the counting detection region.

Hereinafter, a control method of the CT apparatus according to an exemplary embodiment will be described.

In the control method of the CT apparatus according to an exemplary embodiment, a subject of control may be the CT apparatus 100 according to the above-described embodiments. Therefore, the description of the above-described CT apparatus 100 may be applied to a control method of the CT apparatus according to an exemplary embodiment.

Figure 18:
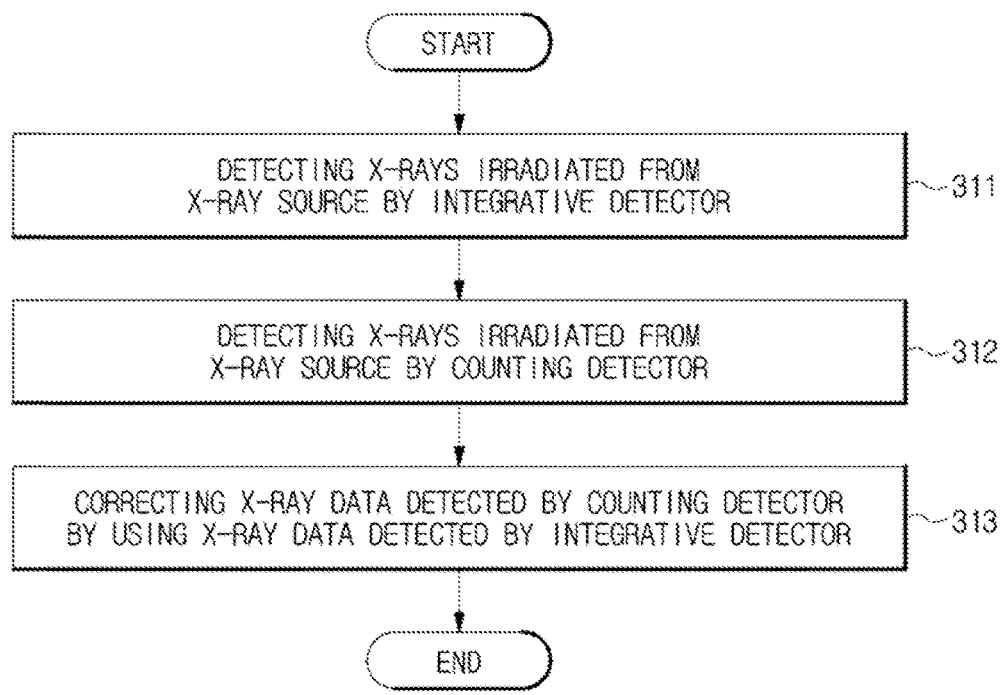
FIG. 18 is a flow chart illustrating a control method of a CT apparatus according to an exemplary embodiment.

FIG. 18 is a flow chart illustrating a control method of a CT apparatus according to an exemplary embodiment.

Referring to FIG. 18, X-rays irradiated from the X-ray source 111 may be detected by the integrative detection region 121a (operation 311), and X-rays irradiated from the X-ray source 111 may be also detected by the counting detection region 121b (operation 312).

Detecting by the integrative detection region 121a and detecting by the counting detection region 121b are described in order due to the feature of flow chart, but there is no sequence between those detecting, and thus those detecting may be performed at the same time.

When X-rays are detected by the integrative detection region 121a, an electrical signal corresponding to the intensity of the detected X-ray may be generated in the integrative detector element 20a constituting the integrative detection region 121a and then transferred to the data obtainer 122. The data obtainer 122 may convert the transferred electrical signal into X-ray data in digital form to transfer to the image processor 130 through the data collector 123.

When X-rays is detected by the counting detection region 121b, a signal (the number of photons) corresponding to the intensity of the detected X-ray may be generated in the counting detector element 20b constituting the counting detection region 121b and then transferred to the data obtainer 122. The data obtainer 122 may convert the transferred signal into X-ray data in digital form to transfer to the image processor 130 through the data collector 123.

By using X-ray data detected through the integrative detection region 121a, X-ray data detected through the counting detection region 121b may be corrected (operation 313).

According to a structure of the detector assembly 120 applied to a control method of the CT apparatus in accordance with an exemplary embodiment, the same quality beam may be incident on the integrative detection region 121a and the counting detection region 121b, and thus the accuracy of calibration may be enhanced by using data acquired from each region.

As apparent from the above description, according to the exemplary CT apparatus and the control method thereof, different kind of detection region, i.e., an integrative detection region and a counting detection region are included in a single detector assembly so that the advantages of each detection region may be used collectively and thus the response characteristics of the detector may be improved.

In addition, by disposing the counting detection region on the center in the Z-axis direction, and the integrative detection region on an inner and outer portions, scan may be performed regardless of a size of an object and a region of interest, and X-ray beam having the same quality may be incident on each detection region so that the accuracy of calibration of data may be improved.

The foregoing exemplary embodiments and advantages are merely exemplary and are not to be construed as limiting. Also, the description of the exemplary embodiments is intended to be illustrative, and not to limit the scope of the claims, and many alternatives, modifications, and variations will be apparent to those skilled in the art.

What is claimed is:

1. A computed tomography (CT) apparatus comprising:
an X-ray source configured to generate X-rays;
a detector which is configured to detect the X-rays radiated by the X-ray source, and comprises:
   a counting detection region configured to generate X-ray data corresponding to the detected X-rays according to a photon counting method, and
   an integrative detection region, which is configured to generate X-ray data corresponding to the detected X-rays according to a charge integration method, and is formed on an outer portion of the counting detection region with respect to a rotation axis of a gantry; and
an image processor configured to calculate a calibration function representing a relationship between the X-ray data acquired by the integrative detection region and the X-ray data acquired by the counting detection region, and obtain an image of an object by acquiring an object X-ray data from the counting detection region, acquiring an object X-ray data from the integrative detection region, and correcting the object X-ray data acquired from the counting detection region by scanning the object based on the calibration function, wherein the image processor is further configured to calculate the calibration function based on the X-ray data which are acquired by the integrative detection region and the counting detection region in a first operation, and correct the object X-ray data acquired from the counting detection region that is acquired by scanning the object in a second operation which is different from the first operation and performed subsequent to the first operation, the gantry includes a bore into which the object is moved for scanning, and the first operation is performed by acquiring X-rays from the bore without any object located therein, to acquire the X-ray data to be used in a calculation of the calibration function.

2. The CT apparatus of claim 1, wherein the detector further comprises:

detection modules which are arranged parallel to one another in a direction perpendicular to the rotation axis, and comprise the counting detection region and the integrative detection region which is formed at the outer portion of the counting detection region with respect to the rotation axis of the gantry.

3. The CT apparatus of claim 2, wherein the detection modules comprise detector elements arranged in two-dimensional (2D) matrices.

4. The CT apparatus of claim 1, further comprising:

a filter mounted between the X-ray source and the detector, wherein at least one among a thickness and a material of the filter is adjustable, in a direction of the rotation axis or in a direction perpendicular to the rotation axis.

5. The CT apparatus of claim 1, wherein the counting detection region is configured to detect the X-rays and generate the X-ray data, by differentiating the detected X-rays by energy bands.

6. The CT apparatus of claim 4, wherein the filter has at least one among a variable thickness and a variable material in the direction perpendicular to the rotation axis, and the image processor is further configured to calculate the calibration function based on the X-ray data generated by acquiring X-rays, which penetrate the at least one among the variable thickness and the variable material of the filter and are incident on the integrative detection region, and acquiring X-rays, which penetrate the at least one among the variable thickness and the variable material of the filter and are incident on the counting detection region, so that the X-rays having a same beam quality are incident on the integrative detection region and the counting detection region.

7. The CT apparatus of claim 5, wherein the detector comprises detector elements, and each of the detector elements placed in the counting detection region comprises a number of comparators and counters in correspondence to a number of the energy bands.

8. A control method of a computed tomography (CT) apparatus comprising a detector, the control method comprising:

acquiring X-ray data from a counting detection region disposed in a center portion of the detector with respect to a rotation axis of a gantry including a bore;

acquiring X-ray data from an integrative detection region disposed on an outer portion of the detector with respect to the center portion, in a direction of the rotation axis;

calculating a calibration function representing a relationship between the X-ray data acquired by the integrative detection region and the X-ray data acquired by the counting detection region; and obtaining an image of an object by acquiring an object X-ray data from the counting detection region, acquiring an object X-ray data from the integrative detection region, and correcting the object X-ray data acquired from the counting detection region by scanning the object based on the calibration function, wherein the calculating the calibration function comprises:

calculating the calibration function based on the X-ray data which are acquired by the integrative detection region and the counting detection region in a first operation, and correcting the object X-ray data acquired from the counting detection region that is acquired by scanning the object in a second operation which is different from the first operation and performed subsequent to the first operation, and wherein the first operation is performed by acquiring X-rays from the bore without any object located therein, to acquire the X-ray data to be used in a calculation of the calibration function.

9. The control method of claim 8, wherein the calculating the calibration function further comprises:

calculating the calibration function based on the X-ray data generated by acquiring X-rays having a same beam quality with respect to each other, among the X-rays incident on the counting detection region and the X-rays incident on the integrative detection region.

* * * * *